United States Patent [19]

Carduck et al.

[11] Patent Number: 5,062,997

[45] Date of Patent: Nov. 5, 1991

[54] PROCESS FOR THE CHLORINATION AND SULFOCHLORINATION OF ORGANIC COMPOUNDS

[75] Inventors: Franz-Josef Carduck, Haan; Willi Wuest, Ratingen-Hoesel; Hubert Harth, Duesseldorf; Harald Liebs, Leverkusen, all of Fed. Rep. of Germany

[73] Assignee: Henkel Kommanditgesellschaft auf Aktien, Duesseldorf, Fed. Rep. of Germany

[21] Appl. No.: 941,590

[22] Filed: Dec. 16, 1986

Related U.S. Application Data

[63] Continuation of Ser. No. 729,313, May 1, 1985, abandoned.

[30] Foreign Application Priority Data

May 5, 1984 [DE] Fed. Rep. of Germany ....... 3416668

[51] Int. Cl.$^5$ ............................................ C07C 303/10
[52] U.S. Cl. .................................... 260/400; 260/408
[58] Field of Search ................................. 260/400, 408

[56] References Cited

U.S. PATENT DOCUMENTS

| | | | |
|---|---|---|---|
| 2,202,791 | 5/1940 | Fox et al. | 260/400 |
| 3,988,247 | 10/1976 | Dieckelmann et al. | 252/8.7 |
| 4,086,256 | 4/1978 | Tsuto et al. | 260/400 |
| 4,451,261 | 5/1984 | Willmund et al. | 252/8.57 |
| 4,451,261 | 5/1984 | Willmund et al. | 8/94.22 |

FOREIGN PATENT DOCUMENTS 3018176 11/1981 Fed. Rep. of Germany .

Primary Examiner—Charles F. Warren
Attorney, Agent, or Firm—Ernest G. Szoke; Wayne C. Jaeschke; Mark A. Greenfield

[57] ABSTRACT

An improvement in the process for chlorination and sulfochlorination of liquid or dissolved organic components, wherein the gases are intensively mixed with the liquid organics until substantially no gases remain unmixed, and the mixture is then reacted.

34 Claims, 2 Drawing Sheets

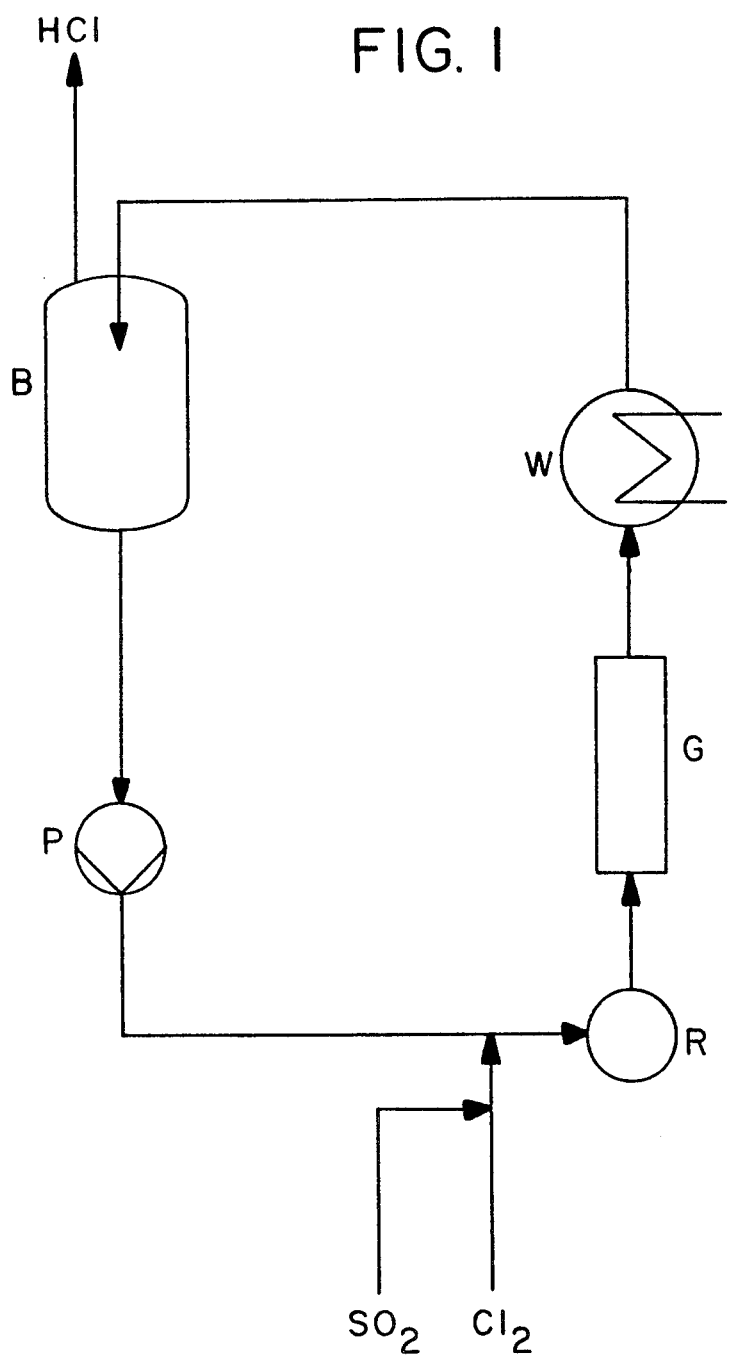

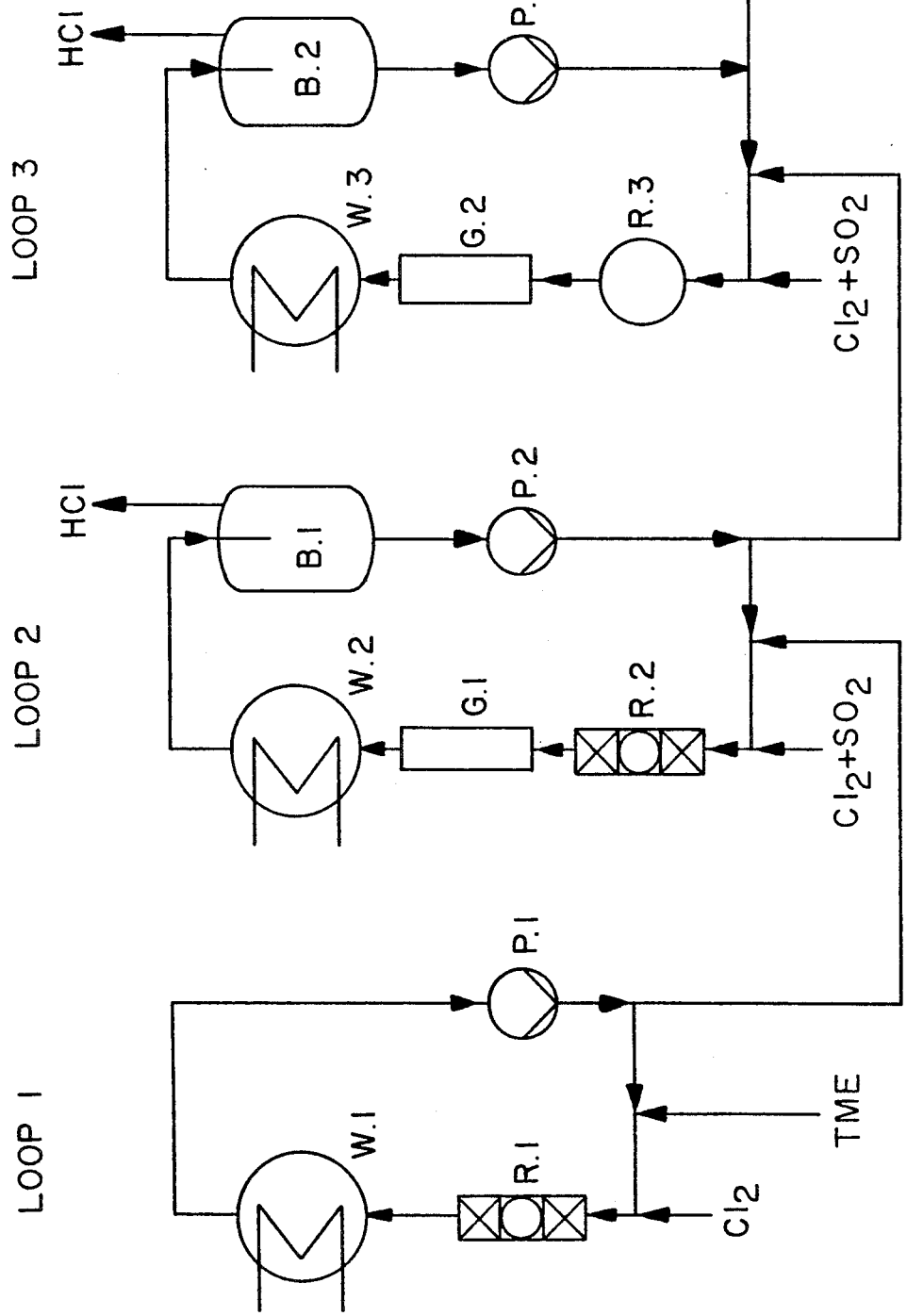

PROCESS FOR THE CHLORINATION AND SULFOCHLORINATION OF ORGANIC COMPOUNDS

This application is a continuation of application Ser. No. 729,313, filed May 1, 1985.

BACKGROUND OF THE INVENTION

1. Field of the Invention

This invention relates to an improved process for reacting chlorine and mixtures of chlorine and sulfur dioxide with liquid or dissolved organic components. The process is particularly advantageous when the liquid phase to be treated shows or assumes an increased viscosity under reaction conditions. The process according to the invention is particularly suitable for the chlorination and sulfochlorination of fatty raw materials particularly fatty acids and/or esters thereof with monohydric and/or polyhydric alcohols. In the context of the invention, chlorination is understood to be both the addition of chlorine onto olefinic double bonds of the starting material and also the HCl-forming substitution reaction optionally activated by UV-light. Sulfochlorination is understood in the usual way to be the optionally UV-activated reaction of $SO_2/Cl_2$-mixtures with aliphatic chain constituents to form the $SO_2Cl$-group, the reaction being accompanied by the elimination of HCl.

2. Statement of the Related Art

The chlorination and sulfochlorination of fatty raw materials, particularly fatty acids and/or fatty acid esters, is known to lead to interesting fat-liquoring agents for leather and skins. Thus U.S. Pat. No. 3,988,247 and corresponding German patent 2,245,077 describe fat-liquoring agents such as these based on sulfonated chlorination products of natural or synthetic higher fatty acids or fatty acid esters in the form of their alkali, ammonium or amine salts, which are characterized in that they consist of sulfonated chlorination products which have been obtained by the chlorination of higher fatty acids or of esters of higher fatty acids having $C_{8-24}$ chain lengths up to a chlorine content of from 20 to 45% by weight, the chlorination products containing virtually no more double bonds and the subsequent sulfonation step with $SO_3$ having been carried out up to a content of from 40 to 100 mol % of $SO_3$, based on chlorination product.

Corresponding fat-liquoring agents are also described in published German patent application 30 18 176 and are characterized in that they comprise sulfonated chlorination products which have been obtained by the sulfochlorination at 20 to 90° C. of higher fatty acids or of esters of higher fatty acids having $C_{8-24}$ chain lengths with chlorine and $SO_2$, optionally under UV-light, up to a content of bound chlorine of from 5 to 30% by weight and a content of $SO_2Cl$-groups of from 1 to 20% by weight, the ratio of chlorine atoms to $SO_2Cl$-groups amounting to about 0.7–70:1, preferably 2–20:1, most preferably 2–7:1, followed by hydrolysis of those groups (saponification). An improvement is described in U.S. Pat. No. 4,451,261 (and corresponding German patent application 32 38 741). In this case, the starting materials used for producing the sulfonated chlorination products are higher fatty acid or fatty acid ester mixtures containing unsaturated fractions. In this process, chlorination is initially carried out up to saturation of the double bonds and is followed by sulfochlorination with chlorine and $SO_2$. The subsequent hydrolysis step gives the required fat-liquoring agents.

Chlorine and $SO_2$ are gaseous under the conditions of the chlorination/sulfochlorination reaction. In order to be able to react with the organic reactant, these gaseous components have to be dissolved in the liquid phase. To this end, the gases are normally passed upwards through gas distributors into a liquid column or gaseous and liquid reactants are passed in countercurrent to one another through exchange units, for example packed columns. However, it has been found that the viscosity of the organic liquid phase increases within increasing reaction time. At the same time, mass transfer between the liquid phase and the gas phase is increasingly inhibited. For example, in a column of the liquid reactant into which the gaseous reactants are introduced from below, increasingly larger bubbles which ascend very rapidly are observed with increasing viscosity of the liquid phase indicating a failure to react. The gaseous components delivered to the reactor leave the reactor unreacted to an increasing extent. The reaction velocity falls, influenced by the rate of transfer of the gases into the liquid phase. In the event of simultaneous absorption and reaction of several gases, the different solubility of the gases in the liquid phase affects the course of the reaction.

GENERAL DESCRIPTION OF THE INVENTION

The present invention is based on the surprising observation that, despite the increasingly poor miscibility of the gas and liquid phases during the reaction, homogenization of the reaction mixture can be obtained by the additional application of mechanical forces, particularly at those stages of the reaction in which, basically, the appearance of the mixture of reactants is not indicative of good miscibility.

Accordingly, the present invention relates to a process for the chlorination and sulfochlorination of fatty raw materials which are liquid under reaction conditions, particularly fatty acids and/or esters thereof, by reaction with chlorine and $SO_2$, in which the liquid starting material is circulated through a reaction zone where it is reacted with chlorine and $SO_2$ which are introduced into the circuit, the new process being particularly characterized in that the chlorine and $SO_2$ are introduced in parallel current with the liquid starting materials (as contrasted with countercurrent) and, together with the liquid starting material, are passed through an intensive mixer during or before entry into the reaction zone. The quantity of chlorine and $SO_2$ introduced is measured in such a way that the reaction mixture passes through the reaction zone as a substantially homogeneous liquid phase.

BRIEF DESCRIPTION OF THE DRAWINGS

FIG. 1 is a flow diagram of one embodiment of the inventive process.

FIG. 2 is a flow diagram of a second embodiment& of the inventive process.

DETAILED DESCRIPTION OF THE INVENTION

The principle on which the process according to the invention is based is illustrated in the flow chart in FIG. 1. The liquid to be chlorinated/sulfochlorinated is delivered to the mixer R from the container B by the pump P. Shortly before, or during, entry into R, the gaseous reactant or the corresponding mixture of reactants is introduced into the circulating liquid, preferably through a coaxial pipe. Static and/or active mixing elements introduced into the liquid circuit may be used as the mixing zone, preference being attributed to static mixing elements which, by means of intersecting baffle elements in the mixing zone, produce a highly turbulent zig-zag flow of the gas-liquid mixture.

Under the effect of the intensive mechanical mixing of the gas-liquid phase in the mixer R, the gas phase is completely or substantially completely dissolved in the increasingly viscous liquid phase, despite the short residence time of the reaction mixture in the mixer R. Since the (a) rate of flow of the reactants (b) time of mixing and (c) mixer capability are all variables, among others, it is impractical to set definite mechanical parameters for the mixer or definite process parameters for the mixing step. However, the mixer mechanical capability and mixing process parameters should be such that the gas phase is at least substantially (preferably completely) dissolved in the liquid phase. The preferred embodiment of the invention, the liquid leaving the mixing zone R contains hardly any visible gas bubbles. The gas liquid mixture then passes through the reaction zone G and then through a heat exchanger after which it is returned to the container B and removed as desired. Any HCl formed is given off in the container and may be delivered to a scrubber.

The described procedure enables the reaction to take place in a single-phase, homogeneous medium, affording inter alia the following advantages:

The reaction velocity cannot be limited by the gas-liquid transfer so that the different solubilities of chlorine and $SO_2$ in the liquid phase have no effect upon the course of the reaction. The chlorine and $SO_2$ have the same residence time in the reaction zone, i.e. a narrow residence time spectrum. The residence time of chlorine and $SO_2$ in the reaction zone is determined solely by the liquid circuit. Unreacted gas is unable to penetrate and escape. It is possible to use liquid phases of high viscosity which, hitherto, it has not been possible to deliver economically to the reaction because of the high tendency of the gas phase to escape from the liquid phase. The reaction itself may be carried out at lower temperatures and, thus at correspondingly higher viscosities of the liquid phase which is of advantage, for example in regard to the selectivity of sulfochlorination. Accordingly, viscosity no longer has any bearing upon the choice of the reaction temperature. The sulfochlorination reaction may thus be carried out without difficulty using a mol ratio of chlorine to $SO_2$ of 1:1 without chain chlorination occurring at the same time or significant losses of $SO_2$ being incurred. This is of interest in cases where inexpensive fats having relatively high iodine values are used. With fats such as these, it is possible first to add chlorine onto the olefinic double bond and then to carry out sulfochlorination without chain chlorination. It is known that, for the same chain chlorine content, only half as much chlorine is consumed in the addition reaction as in the substitution reaction.

The process according to the invention is particularly suitable for the chlorination/sulfochlorination of fats such as triglycerides, fatty acids and/or esters thereof, in any mixture. Examples include tallow, tallow fatty acid methyl ester, coconut oil fatty acid last runnings methyl ester, LT last runnings ester, and mixtures thereof.

The invention preferably starts out with higher fatty acids or with higher fatty acid esters, having chain lengths of from $C_8$ to $C_{24}$ and more especially from $C_{10}$ to $C_{20}$, and iodine numbers of from 10 to 120. Mixtures of fatty acids or naturally occurring fats or oils with a proportion of mono- or polyunsaturated fatty acids are preferred. Examples of these fatty acid mixtures are the fatty acid mixtures (or esters thereof) obtained from coconut oil, soya oil, palm kernel oil, cottonseed oil, rape oil, linseed oil, castor oil, sunflower oil, olive oil, neat's foot oil, peanut oil, herring oil, cod-liver oil, shark-liver oil, whale oil, tallow fats or lard. The corresponding naturally occurring fats or oils and naturally occuring wax esters may also be used as starting material for the process of this invention. The crucial factor is that chlorination and sulfochlorination are now no longer hindered by the high viscosity of the corresponding liquid phases or reaction products formed therefrom.

Particularly preferred starting materials are synthetically produced esters of mixtures of saturated and unsaturated fatty acids having chain lengths of from $C_8$ to $C_{24}$ and preferably from $C_{10}$ to $C_{20}$ and iodine numbers of from 10 to 120, for example decane carboxylic acid, palmitic acid, stearic acid, behenic acid, dodecene carboxylic acid, oleic acid, linoleic acid or carboxylic acids produced by the oxidation of paraffin and esters thereof with monohydric $C_{1-4}$-aliphatic alcohols. By virtue of their ready availability, it can also be of advantage to use fatty acid esters which are transesterification products produced from natural, animal or vegetable fats, oils or waxes reacted with the lower monohydric aliphatic alcohols, particularly methanol. Other alcohols suitable for ester formation are polyhydric $C_{2-6}$-aliphatic alcohols, such as ethylene glycol, 1,2-propylene glycol, glycerol, pentaerythritol or sorbitol, or even higher $C_{8-24}$-alcohols, such as decyl or oleyl.

In one preferred embodiment of the invention, the reaction is carried out in the absence of viscosity-reducing diluents. To solve the problem of viscosity in this field, it had already been proposed to obtain improved mass transfer between the gas and liquid phases by using inert viscosity-reducing diluents.

Suitable mixing elements (see R in FIG. 1) are, typically, commercially available rotor-stator machines. In these machines, high speed rotors produce a mechanical shearing effect between rotor and stator. Under this shearing effect, the gas is completely dissolved during its short residence time in the machine. The homogeneous or substantially homogeneous liquid phase leaving the rotor-stator machine is delivered to the reaction zone G which is usually irradiated with a UV-lamp.

In one preferred embodiment of the invention, static mixing elements are used. Static mixing elements are also commercially available. Suitable static mixing elements are, for example, built-in elements of corrugated, multiple-bend intersecting expanded metal blades. A system of intersecting channels such as this imposes a highly turbulent zig-zag flow on the mixture of liquid phase and gaseous reactants. This ensures intensive mixing and, ultimately, homogenization of the reaction phase. For literature on this subject, see W. Tauscher, "Das breite Anwendungsspektrum des statischen Mischers", *Chemische Produktion* 10:10–14 (1977). Suitable static mixing elements are, for example, those made by Gebrueder Sulzer AG, Winterthur, Switzerland, which are marketed under the trademark "SMV".

The following preferred process parameters apply in particular where static mixing elements of this type built into the flow tube are used: Flow rates of the liquid phase in the static mixing zone (based on the empty tube) in the range from 0.1 to 5 m/s, preferably from 0.25 to 2.5 m/s. Preferred length-to-diameter ratio of the mixing zone is in the range 2–20:1. Comparatively short mixing zones ranging in length from about 10 to 50 cm provide the intensive mixing required for the purposes of the invention. The ratio of the quantity of gas introduced to the quantity of liquid in circulation for both the reaction gases, chlorine and $SO_2$, generally amounts to between 0.05 and 500, preferably between 0.1 and 100, and most preferably between 0.3 and 30, parts by weight of gas to 1,000 parts by weight of liquid.

The chlorine and sulfur dioxide may be introduced either as gaseous reactants or under pressure as liquids into the circulating stream of liquid reactant, in which case they either evaporate or are dispersed and dissolved as liquid, depending on the temperature and pressure prevailing at the point of introduction. The pressure prevailing at the point of introduction of the chlorine and/or sulfur dioxide is typically from 0.2 to 80 bars, preferably 0.2 to 25 bars, most preferably 0.5 to 5 bars.

If a multiple-stage procedure is adopted in accordance with another embodiment of the invention, i.e. if the addition of chlorine onto the olefinic double bonds present takes place in a first stage, followed in a second stage by sulfochlorination, it can be of advantage to carry out the addition of chlorine at a temperature of about 50 to 70° C. and the sulfochlorination step at a temperature of about 30 to 50° C.

The reaction generally lasts for about 2 to 10 hours, by which time from 5 to 30% by weight of chlorine and from 1 to 20% by weight of $SO_2Cl$ groups have been added. The ratio of chlorine atoms to $SO_2Cl$ groups is typically about 0.7–70:1, preferably about 2–20:1, most preferably about 3–7:1.

Subsequent hydrolysis, such as with aqueous, approximately 30% sodium-potassium hydroxide solution, at around 70° C. gives liquid highly concentrated water-emulsifiable products characterized by excellent stability to oxidation, light, and acids which are eminently suitable, for example, for the fat liquoring of leather, as described in detail in above-mentioned U.S. Pat. No. 4,451,261.

The following Examples describe both the addition of chlorine to the olefinic double bonds present and also sulfochlorination in a mol ratio of 1:1, optionally followed by substitution by chlorine at relatively high viscosities.

EXAMPLE 1

841 kg of tallow fatty acid methyl ester (TME) at 20° C., with an Iodine Value (IV) of 52 are introduced into the container B shown in FIG. 1 and circulated by the pump P at a rate of 15 m³/h. Without switching on a UV-lamp located in the reaction zone G, 54 kg/h of chlorine are introduced, the product temperature rising to 61° C. After its chlorine content has reached 14% by weight, the product is cooled to 40° C. and the UV-lamp in the reaction zone G is switched on. 20 kg/h of chlorine and 18 kg/h of $SO_2$ are then introduced until the $SO_2Cl$ content of the reaction product amounts to 15% by weight. There is no change in the chain chlorine content. The inflow of $SO_2$ is then stopped and the product is chlorinated with 20 kg/h of $Cl_2$ under the same conditions up to a chain chlorine content of 18%. 1250 kg of tallow fatty acid methyl ester sulfochloride are obtained.

During the reaction, the viscosity of the liquid phase rises to 300 mPas at 40° C. Nevertheless, the rotor-stator mixer provided in the mixing zone R prevents the formation of any gas bubbles in the circulating liquid phase behind the mixer when it is in operation. If, however, the rotor-stator machine is switched off, the gas ascends rapidly in the form of fist-size bubbles without dissolving. The waste gas from the vessel B is colored by the penetrating chlorine gas.

EXAMPLE 2

A reaction circuit of the type shown in FIG. 1 is again used. On this occasion, however, a static mixer is installed as the mixing unit R. The static mixer in question is formed by 4 elements of the type marketed under the trademark "SMV 8" by Gebrueder Sulzer AG., Winterthur, Switzerland. The total length of the mixing zone amounts to 20 cm for a diameter of 5 cm, so that the length-to-diameter ratio is 4:1.

432 kg of tallow fatty acid methyl ester (TME) at 20° C. (IV=52) are introduced into the vessel B and pump-recirculated at a rate of 9 m³/h. 98 kg/h of chlorine are introduced, the temperature of the liquid phase rising to 58° C. After its chlorine content has reached 18% by weight, the product is cooled to 41° C., the UV-lamp in the reaction zone G is switched on and 14.2 kg/h of $Cl_2$ and 12.8 kg/h of $SO_2$ are introduced until the $SO_2Cl$-content amounts to 16.2% by weight. There is no change in the chain chlorine content. 652 kg of chlorinated tallow fatty acid methyl ester sulfochloride are obtained.

Under the process conditions, hardly any gaseous reactants can be seen in the pump-recirculated liquid phase after it has passed through the mixing zone R.

EXAMPLE 3

The continuous working of the process is described in the following Example with reference to FIG. 2.

The addition of chlorine onto the olefinic double bonds of the starting material used is carried out in the first reaction loop which consists of the first loop recirculation pump P 1, the first loop static mixer R 1 and the first loop heat exchanger W 1. 5 m³/h of liquid phase at 60° C. are pump-recirculated in the first reaction loop. 260 kg/h of tallow fatty acid methyl ester and 36.4 kg/h of chlorine are continuously introduced and 296.4 kg/h of chlorinated tallow fatty acid methyl ester are removed and delivered to the second reaction loop in which sulfochlorination and chlorination take place simultaneously. In the second loop, 9 m³/h of liquid phase at 40° C. are pump-recirculated in the first stage of the sulfochlorination/chlorination process which consists of the second loop recirculation pump P 2, the second loop static mixer R 2, the second loop reaction zone with UV-lamp G 1, the second loop heat exchanger W 2 and the second loop separator B 1. 51.9 kg/h of $Cl_2$ and 20.8 kg/h of $SO_2$ are continuously introduced and 342.4 kg/h of chlorinated tallow fatty acid methyl ester sulfochloride are run off towards the third loop. At the same time, 26.7 kg/h of HCl gas leave the second loop separator B 1.

The third reaction loop consists of a recirculation pump P 3, a third loop mixer R 3, a third loop reaction zone with UV-lamp G 2, a third loop heat exchanger W 3, and a third loop separator B 2, which taken together effectuate the second stage of the sulfochlorination/-chlorination process. The third loop mixer R 3 used in the second stage of the sulfochlorination/chlorination process is a rotor-stator machine. 15 m³/h of liquid phase at 40° C. are pump-recirculated and 46.8 kg/h of Cl₂ and 18.2 kg/h of SO₂ are continuously introduced. 24.1 kg/h of HCl gas are separated in the third loop separator B 2. 383.3 kg/h of chlorinated tallow fatty acid methyl ester sulfochloride containing 16.7% by weight of chain chlorine and 15.8% by weight of SO₂Cl are obtained.

We claim:

1. In a process for the chlorination and sulfochlorination of starting materials which are fatty acids and/or their esters containing olefinically unsaturated fractions and which are liquid under reaction conditions, by reaction with chlorine and SO₂, in which the liquid starting material is circulated through a reaction zone where it is reacted with chlorine and SO₂ which have been introduced into the circuit, the improvement wherein the chlorine and SO₂ are introduced in parallel current with the liquid starting material and, together with the liquid starting material, are passed through an intensive mixing step during or before entry into the reaction zone, the quantity of chlorine and SO₂ introduced being such that the reaction mixture passes through the reaction zone as a substantially homogeneous liquid phase, wherein the process is conducted in two reaction loops, the first loop effecting chlorination of the olefinic double bonds and the second loop effecting the subsequent sulfochlorination, both of said reaction loops having an intensive mixing step during or before entry into their respective reaction zones.

2. The process of claim 1 wherein said second reaction loop is repeated as a third reaction loop, itself having an intensive mixing step during or before entry into its reaction zone.

3. The process of claim 1 wherein said first reaction loop comprises: introducing the liquid starting material into a first loop conduit; introducing the chlorine into said conduit; passing said liquid starting material and said chlorine through a first intensive mixing step, and passing said mixed material through a first cooling means, said reaction loop being repeated until a desired amount of chlorination is effected across said olefinic double bonds.

4. The process of claim 2 wherein said first reaction loop comprises: introducing the liquid starting material into a first loop conduit; introducing the chlorine into said conduit; passing said liquid starting material and said chlorine through a first intensive mixing step, and passing said mixed material through a first cooling means, said reaction loop being repeated until a desired amount of chlorination is effected across said olefinic double bonds.

5. The process of claim 3 wherein said second reaction loop comprises: introducing the chlorinated starting material from said second reaction loop into a second loop conduit; introducing the SO₂ and additional chlorine into said second conduit; passing said chlorinated starting material, SO₂, and additional chlorine through a second intensive mixing step; passing the mixed materials through a first reaction zone, passing the reacted mixture through a second cooling means; and passing the cooled reacted mixture into a first separator wherein any second loop reaction generated HCl by-product is removed.

6. The process of claim 4 wherein said second reaction loop comprises: introducing the chlorinated starting material from said second reaction loop into a second loop conduit; introducing the SO₂ and additional chlorine into said second conduit; passing said chlorinated starting material, SO₂, and additional chlorine through a second intensive mixing step; passing the mixed materials through a first reaction zone, passing the reacted mixture through a second cooling means; and passing the cooled reacted mixture into a first separator wherein any second loop reaction generated HCl by-product is removed.

7. The process of claim 6 wherein said third reaction loop comprises: introducing the chlorinated and sulfochlorinated starting material from the separator of said second reaction loop into a third loop conduit; introducing additional SO₂ and still additional chlorine into said conduit; passing said chlorinated and sulfochlorinated starting material, additional SO₂ and still additional chlorine through a third intensive mixing step; passing the mixed materials through a second reaction zone; passing the reacted mixture through a third cooling means; passing the cooled reacted mixture into a second separator wherein any third loop reaction generated HCl by-product is removed; and removing the finished chlorinated and sulfochlorinated product.

8. The process of claim 5 wherein said mixing means are static mixers, moving mixers, or a combination thereof.

9. The process of claim 7 wherein said mixing means are static mixers, moving mixers, or a combination thereof.

10. The process of claim 5 wherein said first mixing means and said second mixing means are each a static mixer having intersecting baffles which impose a highly turbulent zig-zag flow pattern on the materials being mixed.

11. The process of claim 7 wherein said first mixing means and said second mixing means are each a static mixer having intersecting baffles which impose a highly turbulent zig-zag flow pattern on the materials being mixed and said third mixing means is a moving mixer.

12. The process of claim 1 wherein said introduction of chlorine and SO₂ are by means of a single reaction loop comprising: introducing the liquid starting material into a container; conducting the liquid starting material from said container to an intensive mixing step; introducing said chlorine and SO₂ into said conduit prior to, or upon, entry of said conduit into said intensive mixing step; passing the mixed starting material, chlorine, and SO₂ to a reaction zone; passing the reacted mixture through a cool means; and returning the cooled reacted mixture to said container wherein any reaction generated HCl by-product is removed; said reaction loop being repeated until a desired degree of sulfochlorination is achieved.

13. The process of claim 12 wherein said mixing means is a static mixer having intersecting baffles which impose a highly turbulent zig-zag flow pattern on the materials being mixed.

14. The process of claim 10 wherein each said static mixer has a rate of flow of the liquid phase of about 0.1–5 m/sec based on the empty tube, and the length:diameter ratio of the mixing zone is about 2–20:1.

15. The process of claim 11 wherein each said static mixer has a rate of flow of the liquid phase of about 0.1–5 m/sec based on the empty tube, and the length:diameter ratio of the mixing zone is about 2–20:1.

16. The process of claim 13 wherein each said static mixer has a rate of flow of the liquid phase of about 0.1–5 m/sec based on the empty tube, and the length:diameter ratio of the mixing zone is about 2–20:1.

17. The process of claim 14 wherein said rate of flow is about 0.25–2.5 m/sec.

18. The process of claim 15 wherein said rate of flow is about 0.25–2.5 m/sec.

19. The process of claim 16 wherein said rate of flow is about 0.25–2.5 m/sec.

20. The process of claim 5 wherein the weight ratio of the quantity of gas introduced to the quantity of circulating liquid, for both gaseous reactants, is about 0.00005–0.5:1.

21. The process of claim 7 wherein the weight ratio of the quantity of gas introduced to the quantity of circulating liquid, for both gaseous reactants, is about 0.00005–0.5:1.

22. The process of claim 12 wherein the weight ratio of the quantity of gas introduced to the quantity of circulating liquid, for both gaseous reactants, is about 0.00005–0.5:1.

23. The process of claim 17 wherein the weight ratio of the quantity of gas introduced to the quantity of circulating liquid, for both gaseous reactants, is about 0.0001–0.1:1.

24. The process of claim 18 wherein the weight ratio of the quantity of gas introduced to the quantity of circulating liquid, for both gaseous reactants, is about 0.0001–0.1:1.

25. The process of claim 19 wherein the weight ratio of the quantity of gas introduced to the quantity of circulating liquid, for both gaseous reactants, is about 0001–0.1:1.

26. The process of claim 1 wherein the liquid starting material is esters of $C_{8-24}$ fatty acids or their mixtures, with monohydric alcohols, polyhydric alcohols, or their mixtures.

27. The process of claim 26 wherein said fatty acids are of natural origin.

28. The process of claim 23 wherein the liquid starting material is esters of $C_{8-24}$ fatty acids or their mixtures, with monohydric alcohols, polyhydric alcohols, or their mixtures.

29. The process of claim 24 wherein the liquid starting material is esters of $C_{8-24}$ fatty acids or their mixtures, with monohydric alcohols, polyhydric alcohols, or their mixtures.

30. The process of claim 25 wherein the liquid starting material is esters of $C_{8-24}$ fatty acids or their mixtures, with monohydric alcohols, polyhydric alcohols, or their mixtures.

31. The process of claim 20 wherein the mol ratio of chlorine:$SO_2$ in the sulfochlorination loop is about 1:1.

32. The process of claim 21 wherein the mol ratio of chlorine:$SO_2$ in the sulfochlorination loop is about 1:1.

33. The process of claim 31 wherein the first loop addition of chlorine across said olefinic double bonds is at a temperature of about 50–70° C. and the second loop sulfochlorination is at a temperature of about 30–50° C.

34. The process of claim 31 wherein the first loop addition of chlorine across said olefinic double bonds is at a temperature of about 50–70° C., and the second loop and third loop sulfochlorinations are each a temperature of about 30–50°.

* * * * *